US007887859B2

(12) United States Patent
Friedlaender et al.

(10) Patent No.: US 7,887,859 B2
(45) Date of Patent: Feb. 15, 2011

(54) METHODS OF TREATING EPIPHORA

(75) Inventors: Mitchell H. Friedlaender, La Jolla, CA (US); Harun Takruri, Newport Beach, CA (US)

(73) Assignee: Riolan Technologies, Inc., La Jolla, CA (US)

( * ) Notice: Subject to any disclaimer, the term of this patent is extended or adjusted under 35 U.S.C. 154(b) by 396 days.

(21) Appl. No.: 11/979,355

(22) Filed: Nov. 1, 2007

(65) Prior Publication Data

US 2008/0145459 A1 Jun. 19, 2008

Related U.S. Application Data

(60) Provisional application No. 60/856,007, filed on Nov. 2, 2006.

(51) Int. Cl.
*A61K 36/28* (2006.01)
*A61K 31/125* (2006.01)
*A61K 31/00* (2006.01)

(52) U.S. Cl. .............................. 424/764; 514/692; 514/1

(58) Field of Classification Search .................. None
See application file for complete search history.

(56) References Cited

U.S. PATENT DOCUMENTS

| 5,073,366 A | 12/1991 | Beck |
| 5,182,105 A | 1/1993 | Takata et al. |
| 5,948,414 A | 9/1999 | Wiersma |
| 6,572,849 B2 | 6/2003 | Shahinian |
| 2006/0068040 A1 | 3/2006 | Nair |

FOREIGN PATENT DOCUMENTS

JP 11029482 A * 2/1999

WO WO 9400108 A1 * 1/1994

OTHER PUBLICATIONS

"MedicineNet.com: Propylene glycol-polyethylene glycol gel-nasal". Internet Archive Date: Mar. 23, 2005 [Retrieved from the Internet on: Mar. 10, 2010]. Retrieved from: <http://web.archive.org/web/20050323115236/http://www.medicinenet.com/propylene_glycol-polyethylene_glycol_gel-nasal/article.htm>.*
Bandla, H.P.R., et al., "Lipoid Pneumonia: A Silent Complication of Mineral Oil Aspiration," *Pediatrics 103*, 4 pages, American Academy of Pediatrics (1999).
Malahyde Information Systems, "Vicks Decongestant Nasal Spray," available online at http://www.intekom.com/pharm/procter/vick-dns.html, 2 pages, Malahyde Information Systems (accessed on Jun. 2006).
Procter & Gamble, S.A. Ltd., "VapoRub Ointment," available online at http://vicks.com/products/vapor_rubointment.shtml, 3 pages, Procter & Gamble, S.A. Ltd. (accessed on Jun. 2006).
Spickard, A. and Hirschmann, J.V., "Exogenous Lipoid Pneumonia,"*Arch. Intern. Med. 154*:686-692, American Medical Association (1994).
Virtual Medical Centre, "Oxymetazoline hydrochloride 0.05%, Eucalyptol 0.02%, Menthol 0.012%w/w," available online at http://www.virtualrespiratorycentre.com/drugs.asp?drugid=1345&type=generic, 2 pages, Virtual Medical Centre (2003).
International Search Report for International Application No. PCT/US07/23029, mailed Apr. 7, 2008, ISA/US, Virginia, U.S.A.
Written Opinion of the International Searching Authority for International Application No. PCT/US07/23029, mailed Apr. 7, 2008, ISA/US, Virginia, U.S.A.
Report from *Traditional Knowledge Digital Library* (*TKDL*), Council of Scientific & Industrial Research, New Delhi, India, 52 pages (before 1959), EPO-DG Report date (stamped): Oct. 15, 2009.

* cited by examiner

*Primary Examiner*—Amy L Clark
(74) *Attorney, Agent, or Firm*—Sterne, Kessler, Goldstein & Fox, P.L.L.C.

(57) ABSTRACT

The present invention is related to a method for treating epiphora, the method comprising administering to a nasal area of a subject in need thereof a composition comprising camphor, eucalyptus oil, and menthol, wherein the composition is substantially free of lipids other than the eucalyptus oil.

21 Claims, No Drawings

METHODS OF TREATING EPIPHORA

This application claims the benefit of the filing date of U.S. Appl. No. 60/856,007, filed Nov. 2, 2006, the entirety of which is fully incorporated by reference herein.

BACKGROUND OF THE INVENTION

1. Field of the Invention

The present invention is related to methods of treating epiphora, the methods comprising administering to a nasal area or ocular area of a subject in need thereof a composition comprising camphor, eucalyptus oil, and menthol, wherein the composition is substantially free of lipids other than the eucalyptus oil.

2. Background Art

Tears are continuously produced by the lacrimal and accessory lacrimal glands, and bathe the eye with a complex fluid consisting of aqueous, mucinous, and oily components. Tears drain through the lacrimal puncta, small openings at the inner edge of the upper and lower eyelids, through canals (the canaliculi), into the nasolacrimal duct, and finally into the nose. Excessive tearing, or watering of the eyes, is known as "epiphora." Epiphora is a common condition, especially in some populations, e.g., senior citizens, allergic individuals, and people with rosacea and/or blepharitis. The most common causes of epiphora are nasal congestion, laxity of the lower eyelid (ectropion), and turning out of the tear drainage duct (punctal ectropion). These causes are usually associated with inadequate, or misdirected, drainage of naturally-produced tears. If there is blockage, or a narrowing, of the tear drainage system, clearance of tears can be impaired, and the tears can "back up," accumulate in the eyes, or run down the face.

In some instances, epiphora is due to excessive production of tears. Excessive production of tears can occur when the eyes are irritated by chemical, mechanical, and biological stimuli (such as allergens, and microbial agents). Excessive tearing can also be caused by irritation of the eye from debris on the eyelids, or from misdirected eye lashes.

When epiphora is caused by impaired drainage into the nose, the condition can be improved or corrected by opening the nasal passages, either pharmacologically or mechanically. Pharmacologic opening can be accomplished with nasal sprays, such as oxymetazoline hydrochloride, 0.05%, or oral decongestants, such as pseudoephedrine hydrochloride. Improved drainage can also be accomplished mechanically, by probing, dilating, and irrigating the nasolacrimal system.

Other treatments for epiphora can include administration of antibiotic eye drops or ointments, surgery to correct an eyelid deformity, or removal a foreign body. In some severe cases, an obstruction of the nasolacrimal duct can be treated by a procedure called a "dacryocystorhinostomy" (DCR). During the DCR procedure, the obstruction in the nasolacrimal duct is bypassed by creating a new drainage pathway. A temporary tube is then left in place to keep the new passage from scarring and closing.

A need exists in the art for additional methods of treating epiphora. For example, a need exists for a method of treating epiphora that is safe, easy, and effective, and which in some instances does not require a visit to a medical professional.

BRIEF SUMMARY OF THE INVENTION

The present invention is directed to a method for treating epiphora, the method comprising administering to a nasal area or ocular area of a subject in need thereof a composition comprising camphor, eucalyptus oil, and menthol, wherein the composition is substantially free of lipids other than the eucalyptus oil.

In some embodiments, the composition is a gel, cream, ointment, jelly, lotion, or viscous liquid. In some embodiments, the composition further comprises a viscosity modifying agent. For example, the viscosity modifying agent can be selected from the group consisting of polyethylene glycol, polyvinyl alcohol, gelatin, hyaluronic acid, carbomer, tragacanth, soluble cellulose derivatives, colloidal magnesium aluminum silicate, sodium alginate, and combinations thereof. In some embodiments, the viscosity modifying agent is polyethylene glycol. For example, the polyethylene glycol can be selected from the group consisting of polyethylene glycol 200, polyethylene glycol 300, polyethylene glycol 400, polyethylene glycol 600, polyethylene glycol 900, polyethylene glycol 1000, polyethylene glycol 1450, polyethylene glycol 3350, polyethylene glycol 4500, polyethylene glycol 8000, and combinations thereof. In some embodiments, the viscosity modifying agent is about 10% to about 99% (w/w) of the composition, about 50% to about 95% (w/w) of the composition, or about 75% to about 95% (w/w) of the composition.

In some embodiments, the camphor is about 1% to about 10% (w/w) of the composition, or about 4% to about 6% (w/w) of the composition.

In some embodiments, the eucalyptus oil is about 0.5% to about 5% (w/w) of the composition, or about 1% to about 2% (w/w) of the composition.

In some embodiments, the menthol is about 1% to about 10% (w/w) of the composition, or about 2% to about 4% (w/w) of the composition.

In some embodiments, the composition is water soluble.

In the present invention, in some embodiments, the composition further comprises an excipient. In some embodiments, the excipient is about 0.05% to about 20% (w/w) of the composition, about 0.05% to about 5% (w/w) of the composition, or about 2% to about 10% (w/w) of the composition.

In some embodiments, the composition further comprises a mucoadhesive. For example, in some embodiments, the mucoadhesive is selected from the group consisting of hydroxypropyl cellulose, hydroxypropyl methylcellulose, hydroxy ethylcellulose, ethylcellulose, carboxymethyl cellulose, dextran, guar gum, polyvinyl pyrrolidone, a pectin, a starch, gelatin, casein, an acrylic acid polymer, a polymer of acrylic acid ester, an acrylic acid copolymer, a vinyl polymer, a vinyl copolymer, a polymer of vinyl alcohol, an alkoxy polymer, a polyethylene oxide polymer, a polyether, and combinations thereof.

In some embodiments, the method comprises administering the composition of the invention to a nasal area wherein the composition is applied to a nasal cavity, external nare, upper lip, philtrum, or combination thereof of the subject in need thereof.

In some embodiments, the method of the present invention comprises administering to an ocular area of a subject in need thereof a composition comprising camphor, eucalyptus oil, and menthol, wherein the composition is substantially free of lipids other than the eucalyptus oil. In some embodiments, the composition comprises (a) about 0.004% to about 0.4% (w/v) camphor; (b) about 0.001% to about 0.5% (w/v) eucalyptus oil; and (c) about 0.001% to about 0.5% (w/w) menthol. In some embodiments, the composition is a liquid.

In some embodiments, the composition comprises: (a) about 1.0% to about 10% (w/w) camphor; (b) about 0.05% to about 5% (w/w) eucalyptus oil; and (c) about 1.0% to about 10% (w/w) menthol. In some embodiments, the composition comprises: (a) about 1.0% to about 10% (w/w) camphor; (b)

about 0.05% to about 5% (w/w) eucalyptus oil; (c) about 1.0% to about 10% (w/w) menthol; and (d) about 75% to about 97.5% (w/w) polyethylene glycol, wherein the composition is substantially free of lipids other than the eucalyptus oil.

In some embodiments, the composition comprises (a) about 4.8% (w/w) camphor; (b) about 1.2% (w/w) eucalyptus oil; (c) about 2.6% (w/w) menthol; (d) about 30% (w/w) polyethylene glycol 3350; and (e) about 61.4% (w/w) polyethylene glycol 300, wherein the composition is substantially free of lipids other than the eucalyptus oil.

In some embodiments, the composition comprises (a) about 4.8% (w/w) camphor; (b) about 1.2% (w/w) eucalyptus oil; (c) about 2.6% (w/w) menthol; (d) about 40% (w/w) polyethylene glycol 3350; (e) about 40% (w/w) polyethylene glycol 300; and (f) about 11.4% (w/w) water, wherein the composition is substantially free of lipids other than the eucalyptus oil.

In some embodiment, the present invention is directed to a kit comprising: (a) a composition comprising camphor, eucalyptus oil, and menthol, wherein the composition is substantially free of lipids other than the eucalyptus oil; and (b) instructions for using the composition of (a) for the treatment of epiphora.

In some embodiments, the present invention is directed to a means for administering the composition.

In some embodiments, a kit comprises the composition of the present invention, wherein the composition is individually packaged for a single administration.

DETAILED DESCRIPTION OF THE INVENTION

The present invention is directed to a method for treating epiphora, the method comprising administering to a nasal area or ocular area of a subject in need thereof a composition comprising camphor, eucalyptus oil, and menthol, wherein the composition is substantially free of lipids other than the eucalyptus oil.

It is to be noted that the term "a" or "an" refers to one or more of that entity; for example, "a viscosity modifying agent," is understood to represent one or more viscosity modifying agents. As such, the terms "a" (or "an"), "one or more," and "at least one" can be used interchangeably herein. As used herein, "about" refers to plus or minus 10% of the indicated number. For example, "about 0.5%" indicates a range of 0.45% to 0.55%.

Epiphora is the medical term for excessive tearing of the eye. "Watery eyes" is sometimes used as a synonym for epiphora. The most common cause of epiphora is an overflow of tears, usually caused by insufficient drainage of tears from the eye due to a blockage of the nasolacrimal system. The nasolacrimal system comprises the complete drainage system from the eyes to the nose, including the lacrimal puncta, through the canaliculi, into the nasolacrimal duct, and into the nasal cavity. Blockage of the nasolacrimal system can be caused by acquired punctal stenosis, canalicular stenosis or canaliculitis, dacryocystitis or lacrimal sac tumors. Conditions that obstruct tear flow can also include congenital (present at birth) malformation of the tear duct system, foreign bodies, sinus or nasal infections, or inflammation of the tear ducts. Conditions such as allergic conjunctivitis can also cause blockage of the nasolacrimal system. Blockage can be caused by inflammation, injury, or tumors of the nasolacrimal system. Blockage can occur at any point in the nasolacrimal system from the punctum to the nose.

Epiphora can also be associated with increased tear production generally caused by irritation of the eye. Potential irritants include foreign bodies or inward-growing eyelashes. Additionally, eye infections or cancer of the eyelid can cause epiphora.

Epiphora also can result from the inability of the eyelid to blink correctly, which inhibits removal of tears from the surface of the eyeball. Nerve damage, entropion (inward turning of the eyelid), and ectropion (outward turning of the eyelid) are conditions that can interfere with the blinking process. The symptoms of epiphora can be exacerbated by environmental factors such as excessive cold, wind, pollen or other airborne particulate matter, sleep deprivation, eye strain, or emotional stress.

Symptoms of epiphora can include excessive tearing, matting of the eyelashes, and mucous or pus-like discharge from the puncta. Excess tearing can cause infection and, if left untreated, could be detrimental to good vision. In subjects experiencing epiphora, eyelid irritation is common because the area remains wet.

The term "epiphora" can include chronic epiphora and/or acute epiphora. In some embodiments, it is within the scope of the present invention to administer to patients who present with complaints of "excessive tearing," even when this tearing is typically not significant enough to constitute true epiphora. In some embodiments, the present invention is directed to a method of treating a subject presenting with complaints of excessive tearing.

The current invention is directed to a method for treating epiphora, wherein the method treats one or more of the causes or symptoms of epiphora as described herein. However, one of skill in the art will recognize that not all the causes or symptoms of epiphora need to be treated by the method of the present invention.

While not being bound by any particular theory, in some embodiments the method of the invention is believed to treat epiphora by widening the nasolacrimal passages. However, in some embodiments, even subjects whose tearing was caused by excessive tear production, rather than impaired tear drainage, can benefit from the composition of the present invention, since a wider, more efficient drainage system can carry away excessive amounts of tears.

The composition of the present invention can be in any physical state suitable for administration to a nasal area. In some embodiments, the composition is a gel, cream, ointment, jelly, lotion, or viscous liquid. In some embodiments, the composition can be a liquid. In some embodiments, the composition is in a physical form suitable for placement in an inhaler and/or a nasal spray. For example, in some embodiments can be a solid, solution, suspension, or emulsion.

The present invention comprises compositions substantially free of lipids other than the eucalyptus oil. Although oleaginous bases such as petrolatum and petrolatum-based pharmaceutical gels are effective vehicles for camphor, eucalyptus oil and menthol, they are not preferred embodiments since application near the nasal area increases the possibility of lipids migrating into the respiratory system and causing lipoidal pneumonia. Of particular importance are compositions whose vehicles are lipid free, e.g., water-based or water-soluble gels, rather than lipid-based gels.

Lipoidal pneumonia refers to a pulmonary condition marked by inflammatory and fibrotic changes in the lungs due to the inhalation of various lipid substances, e.g. petroleum. Due to the possibility of lipoidal pneumonia, the product information sheet for the topical petroleum-based analgesic Vick's VapoRub® (Proctor and Gamble, Cincinnati, Ohio), which is a product that contain camphor, eucalyptus oil, and menthol, specifically instructs users to apply the product only to the chest and throat. Application of a lipid-based composition to the chest or throat reduces the likelihood that the lipid-based product will get into the lungs.

Application to the chest and throat is sufficient when using Vick's VapoRub® for its analgesic effect, since it is not intended for the treatment of epiphora. However, for treatment of epiphora, application of a composition comprising camphor, eucalyptus oil and menthol closer to the nasolacrimal system is desired. Thus, the present invention overcomes the problems associated with traditional petroleum-based compositions by making a composition wherein the camphor, eucalyptus oil, and menthol are in vehicle substantially free of lipids other than the eucalyptus oil.

The present compositions can be in any physical state suitable to be administered to the nasal or ocular area, such as, but not limited to, liquids (e.g., solutions or suspensions), semi-solids (gels, creams, ointments, etc.), and the like. Each of these physical states of the present compositions can be prepared using techniques and processes which are conventional and well known in the art. For a more detailed discussion of the preparation and administration of ophthalmic formulations see Remington's Pharmaceutical Sciences, 15 Ed., pgs. 1489 to 1504 (1975) which is incorporated in its entirety herein by reference. In some embodiments, the composition is administered in a liquid state. In some embodiments, the composition is administered as a gel, cream or ointment.

In some embodiments, the composition further comprises a viscosity modifying agent. Any viscosity modifying agent suitable for contact with a nasal area can be used. For example, the viscosity modifying agent can be selected from the group consisting of polyethylene glycol, polyvinyl alcohol, gelatin, hyaluronic acid, carbomer, tragacanth, soluble cellulose derivatives, colloidal magnesium aluminum silicate, sodium alginate, and combinations thereof. In some embodiments, the composition does not comprise a viscosity modifying agent.

In some embodiments, the viscosity modifying agent is polyethylene glycol. Any mixture of solid and liquid polyethylene glycols can be substituted in the above formulation to give the desired consistency. In addition the liquid polyethylene glycol component can be replaced partially or completely by suitable amounts of glycerin, propylene glycol, or similar liquid polyols. For example, the polyethylene glycol can be selected from the group consisting of polyethylene glycol 200, polyethylene glycol 300, polyethylene glycol 400, polyethylene glycol 600, polyethylene glycol 900, polyethylene glycol 1000, polyethylene glycol 1450, polyethylene glycol 3350, polyethylene glycol 4500, polyethylene glycol 8000, and combinations thereof.

Various amounts of viscosity modifying agents can be used in the present invention. In some embodiments, the viscosity modifying agent is about 10% to about 99% (w/w) of the composition, about 50% to about 95% (w/w) of the composition, or about 75% to about 95% (w/w) of the composition.

In other embodiments of this invention, water, or other water-based solvents, can be added to the viscosity agent to provide the desired consistency of the composition. Various amounts of water or water-based solvent can be used. In some embodiments, the composition can comprise about 5% to about 50% (w/w) water, about 10% to about 40% (w/w) water, or about 15% to about 30% (w/w) water. By way of example, in some embodiments a vehicle consisting of: 40% PEG 3350, 40% PEG 300 and 20% water can have the right consistency and properties to serve as a vehicle for camphor, eucalyptus oil, and menthol. For compositions of the present invention that are in a liquid state, the compositions can comprise about 50% to 99.9% (v/v) water, about 70% to 99% (v/v) water, or about 80% to about 97% (v/v) water. In some embodiments, the compositions can comprise about 98%, about 98.5%, about 99%, about 99.5%, about 99.8% or about 99.9% water.

In some embodiments, the composition comprises all three of camphor, eucalyptus oil, and/or menthol. In some embodiments of the present invention, the combination of two or three of camphor, eucalyptus oil, and menthol is used to achieve the preferred therapeutic result of treating epiphora. However, one of skill in the art can appreciate that in some embodiments, only one of camphor, eucalyptus oil, and menthol can be sufficient to achieve the therapeutic result of treating epiphora. Thus, in some embodiments of the present invention, the composition comprises one or more of camphor, eucalyptus oil, and/or menthol. For example, in some embodiments, the method of the present invention comprises administering to a nasal area of a subject in need thereof a composition comprising camphor, wherein the composition is substantially free of lipids other than the eucalyptus oil. In some embodiments, the method of the present invention comprises administering to a nasal area of a subject in need thereof a composition comprising menthol, wherein the composition is substantially free of lipids other than the eucalyptus oil. In some embodiments, the method of the present invention comprises administering to a nasal area of a subject in need thereof a composition comprising eucalyptus oil, wherein the composition is substantially free of lipids other than the eucalyptus oil.

The term "camphor," also known as 1,7,7-trimethylbicyclo[2.2.1]heptan-2-one or 2-camphanone, refers to a compound of Formula I or derivatives thereof:

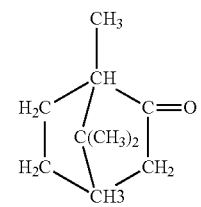

I

Various grades and purities of camphor may be used, as long as they are suitable for use in the composition of the present invention. Various amounts of camphor can be used in the present invention. In some embodiments, the camphor is about 0.1% to about 20% (w/w) of the composition, about 1% to about 10% (w/w) of the composition, or about 4% to about 6% (w/w) of the composition. In some embodiments, the camphor is in a liquid composition, and the camphor is about 0.001% to about 1.0% (w/v) of the composition, about 0.004% to about 0.4% (w/v) of the composition, or about 0.01% to about 0.1% (w/v) of the composition.

The term eucalyptus oil refers to oil derived from a Eucalyptus tree. The components of oils extracted from Eucalyptus trees can vary according to the species from which the oil was harvested, as well as which part of the tree the oil was harvested from (e.g., dry leaves, fresh leaves, buds, mature fruit, bark, etc.). In general, the main chemical components of eucalyptus oil are a-pinene, b-pinene, a-phellandrene, 1,8-cineole, limonene, terpinen-4-ol, aromadendrene, epiglobulol, piperitone and globulol, although one of skill in the art can appreciate that the composition of eucalyptus oil does not require one or more of these components. For example, the same compounds (e.g., 1,8-cineole) exist in many of species, but some compounds can be found in only one or a few species. In some embodiments, eucalyptus oil contains greater than 10% (w/w) 1,8-cineole (eucalyptol), greater than 30% (w/w) 1,8-cineole, greater than 50% (w/w) 1,8-cineole, 50% to 95% (w/w) 1,8-cineole, 60% to 90% (w/w) 1,8-cineole, or 70% to 85% (w/w) 1,8-cineole. In some embodiments, the oil from *E. globulus* or *E. polybractea* is used in the present invention. In some embodiments, the oils comprise a blend of oils from different species of *Eucalyptus*. In some embodiments, the eucalyptus oil is obtained by steam distillation from the fresh leaves of *Eucalyptus globulus* Labillardiere and other species of *Eucalyptus* L'Heritier (Fam. Myrtaceae). In some embodiments, the eucalyptus oil is a commercially available oil, e.g., a eucalyptus oil supplied by Spectrum Chemicals (Gardena, Calif.). In some embodiments, the eucalyptus oil meets Food Chemical Code (FCC) specifications.

Various amounts of eucalyptus oil can be used in the composition of the present invention. In some embodiments, the eucalyptus oil is about 0.1% to about 10% (w/w), about 0.5% to about 5% (w/w) of the composition, or about 1% to about 2% (w/w) of the composition. In some embodiments, the eucalyptus oil is in a liquid composition, and the eucalyptus oil is about 0.0005% to about 1.0% (w/v) of the composition, about 0.001% to about 0.5% (w/v) of the composition, or about 0.01% to about 0.1% (w/v) of the composition.

The term "menthol" refers to a compound of Formula II, and any stereoisomer or derivative thereof.

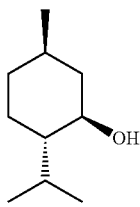

Various grades and purities of menthol can be used in the present invention, as long as they are suitable for use in the composition of the present invention. Various amounts of menthol can be used in the composition of the present invention. In some embodiments, the menthol is about 0.2% to about 20% (w/w) of the composition, about 1% to about 10% (w/w) of the composition, or about 2% to about 4% (w/w) of the composition. In some embodiments, the menthol is in a liquid composition, and the menthol is about 0.0005% to about 1.0% (w/v) of the composition, about 0.001% to about 0.5% (w/v) of the composition, or about 0.01% to about 0.1% (w/v) of the composition.

In the present invention, the composition is substantially free of lipids other than the eucalyptus oil. The term "lipid" refers to hydrocarbon-based molecules of biological origin that are predominantly nonpolar or hydrophobic. The basic classes of lipids are: fatty acids (e.g., saturated or unsaturated fatty acids), glycerides or glycerolipids (e.g., monoglycerides, diglycerides, triglycerides (neutral fats), phosphoglycerides or glycerophospholipids), nonglycerides (e.g. sphingolipids, sterol lipids (includes cholesterol and steroid hormones)), prenol lipids (includes terpenoids), waxes, polyketides, and complex lipid derivatives (e.g., glycolipids, and protein-linked lipids). In some embodiments, the term lipid refers to petrolatum or petroleum. The term "petrolatum" refers to a substance which is a complex combination of semi-solid, saturated hydrocarbons, mainly of a paraffinic nature, obtained from petroleum. Generally, petrolatum comprises liquid hydrocarbons having carbon numbers predominately greater than $C_{25}$. As described previously, the absence of lipids can be beneficial when placing the composition of the present invention to the nasal area to avoid the occurrence of lipoidal pneumonia.

In the present invention, the composition is substantially free of lipids other than the eucalyptus oil, to avoid or reduce the risk of lipoidal pneumonia. In some embodiments, the term "substantially free of lipids" refers to a composition wherein about 0% to 2% (w/w) of the composition is a lipid other than eucalyptus oil, about 0% to 1% (w/w) of the composition is a lipid other than eucalyptus oil, about 0% to 0.5% (w/w) of the composition is a lipid other than eucalyptus oil, or about 0% to 0.2% (w/w) of the composition is a lipid other than eucalyptus oil, or about 0% to 0.1% (w/w) of the composition is a lipid other than eucalyptus oil. In some embodiments, the term "substantially free of lipids" refers to compositions wherein less than 0.1% of the composition is a lipid other than eucalyptus oil.

In some embodiments, the composition is water soluble. The term "water soluble" refers the ability of the composition to dissolve (i.e., form a solution) in water. One of skill in the art will recognize that solubility will be dependent on the volume of the solvent (i.e., water), the presence or absence of other compounds (e.g., solubilizing agents), as well as the temperature of the solvent. In some embodiments, the term "water soluble" refers to the ability of at least 90% of a substance to dissolve completely in water at room temperature in 1 hour, wherein the substance is 10% the volume of the water.

In the present invention, in some embodiments the composition further comprises an excipient. For example, in some embodiments, the excipient is selected from the group consisting of a moisturizer; acid, base or buffering agent; preservative agent; and combinations thereof.

Various moisturizers can be used. In some embodiments, the moisturizer can be selected from the group consisting of water, urea, guanidine, glycolic acid, polyhydroxy alcohols such as sorbitol, glycerin, hexanetriol, propylene glycol, hexylene glycol and the like, polyethylene glycol, sugars and starches, sugar and starch derivatives, D-panthenol, hyaluronic acid, lactamide monoethanolamine, acetamide monoethanolamine, and mixtures thereof.

The composition of the present invention can also include an acid, base or buffering agent (buffers). Acids/bases/buffers can be included to provide and/or maintain the composition at a pH in the physiologically acceptable range, more preferably in a range of about 3 to about 9, or about 4 to about 8.5, still more preferably about 5 to about 8.5 or about 5.5 to about 8.0, and especially about 6.0 to about 8.0 or about 6.5 to about 7.0. As one of skill in the art will recognize, the pH can vary over time, depending on various factors, e.g., stability of the composition, amount of exposure to the atmosphere, strength of buffer, etc. Thus, as used herein, when referring to compositions, kits or methods of the present invention, any specified pH refers to the pH at any time between the time of manufacturing and time of administering.

The term "buffer" or buffering agent refers to a pharmaceutically acceptable compound or composition that is capable of neutralizing both acids and bases and thereby maintaining the original acidity or basicity of the composition. Buffers can include, but are not limited to, phosphate buffers (e.g., sodium and potassium phosphates), phosphates, bicarbonate, citrate, borate, acetate buffers, citrate buffers, tromethamine buffers and combinations thereof. Preferred buffers are selected from the group consisting of citric acid, sodium citrate, boric acid, sodium borate, one or more sodium salts of phosphoric acid, one or more potassium salts of phosphoric acid, sodium bicarbonate, and combinations thereof.

Acids useful in the present compositions can include boric acid, hydrochloric acid, acetic acid, other acids which are ophthalmically acceptable in the concentrations used, and the like.

Bases which can be included in the present compositions include, but are not limited to, sodium and/or potassium hydroxides, other alkali and/or alkaline earth metal hydroxides, organic bases, other bases which are ophthalmically acceptable in the concentrations used, and the like.

In some embodiments, the excipient is a preservative. Typical preservatives include the lower alkyl esters of para-hydroxybenzoates (parabens), especially methylparaben, propylparaben, isobutylparaben and mixtures thereof, benzyl alcohol, phenyl ethyl alcohol, benzoic acid, EDTA, and benzalkonium chloride.

In some embodiments, the excipient is about 0.05% to about 20% (w/w) of the composition, about 0.05% to about 5% (w/w) of the composition, or about 2% to about 10% (w/w) of the composition.

In some embodiments of the present invention, the composition further comprises a mucoadhesive. In some embodiments, the mucoadhesive is selected from the group consisting of hydroxypropyl cellulose, hydroxypropyl methylcellulose, hydroxy ethylcellulose, ethylcellulose, carboxymethyl cellulose, dextran, guar gum, polyvinyl pyrrolidone, a pectin, a starch, gelatin, casein, an acrylic acid polymer, a polymer of acrylic acid ester, an acrylic acid copolymer, a vinyl polymer, a vinyl copolymer, a polymer of vinyl alcohol, an alkoxy polymer, a polyethylene oxide polymer, a polyether, and combinations thereof.

In some embodiments, the method of the present invention comprises administering a composition to a nasal area. It is to be appreciated that the term "administering" refers to the placement of the composition in or in close proximity to the nasal area of the subject being treated. Thus, the term administering would refer to placement of the composition near a nasal area, whether or not there was direct contact between the skin or mucosa of the subject to which the composition is being administered. The term "administering to a nasal area" also refers to placement of the composition of the invention on an apparatus or other object, and then placing the nasal area in close proximity to the composition. For example, "administering to a nasal area" would include a subject who sniffed or breathed in while placing his/her nasal area in close proximity to the composition of the present invention (e.g., sniffing a jar, tube, bottle, etc., filled with the composition of the present invention). In some embodiments, "administering to a nasal area" includes nasally applying the composition of the invention, e.g., from an inhaler or a nasal spray apparatus, optionally while sniffing or inhaling. In some embodiments, the term "administering" refers to the direct placement of the composition of the present invention onto the skin or mucosa of the subject. For example, administering can comprise smearing or spreading the composition on the skin or mucosa of the subject. In some embodiments, administering to a nasal area includes the application of the composition using a nasal swab or other applicator. In some embodiments, the term "administering" refers to the placement of a liquid composition of the present invention to an ocular area (e.g., administering eye drops).

In some embodiments, the term "nasal area" refers to any area on the head of the subject to which the composition is being administered. In some embodiments, the nasal area refers to the face of the subject to which the composition is being administered (e.g., the area of the body between the top of the forehead and the chin, or the area on the face between the two ears). In some embodiments, the nasal area of the present invention comprises a nasal cavity, external nare, upper lip, philtrum, or combination thereof of the subject in need thereof.

In some embodiments of the present invention, the method of treating epiphora comprises administering to an ocular area of a subject in need thereof a composition comprising camphor, eucalyptus oil, and menthol, wherein the composition is substantially free of lipids other than the eucalyptus oil. The term "ocular area" refers to an eye ball surface as well as the external skin surrounding the eye ball, i.e., the eyelid and the margin of the eyelid, and associated hair projecting therefrom, i.e., eyelashes and eye brows. The ocular area can be present on any animal having an eyelid.

The methods of the present invention are applicable to both human use and veterinary use, preferably for human use. In some embodiments, the methods are applicable for use on domesticated animals such as companion animals (dogs and/or cats), livestock, or other economically important animals (e.g., model or breeding animals).

The composition of the present invention can be administered a single time or multiple times throughout the day. For example, the composition can be applied to the nasal mucosa each night, during the day, or at both times. In some embodiments, the composition is administered once daily, twice daily, three times daily, or four times daily. In some embodiments, the composition is administered hourly. In some embodiments, the composition can be administered on an "as needed" or "as desired" basis, as determined by a medical professional or the subject being administered to.

Various amounts of the composition can be administered. One of skill in the art will understand that the amount to be administered is dependent on various factors, e.g., the location of administration, the concentration of the eucalyptus oil, menthol, and camphor, the viscosity or physical state of the composition, the frequency of administration, etc. For example, lower concentrations of camphor, menthol and eucalyptus can be used if the composition is administered to an ocular area compared to if the composition was administered to the nasal cavity. In some embodiments, the amount of the composition to be administered is less than about 10 mL, about 0.1 mL to about 5 mL, about 0.2 mL to about 3 mL, or about 0.5 mL to about 2 mL. In some embodiments, the composition is a liquid, and the amount to be administered is about 1 to 30 drops, about 1 to 20 drops, about 2 to 10 drops, or about 3 to 5 drops.

The composition can comprise camphor, eucalyptus oil, and menthol in various amounts. In some embodiments, the composition comprises: (a) about 1.0% to about 10% (w/w) camphor; (b) about 0.05% to about 5% (w/w) eucalyptus oil; and (c) about 1.0% to about 10% (w/w) menthol. In some embodiments, the composition comprises: (a) about 1.0% to about 10% (w/w) camphor; (b) about 0.05% to about 5% (w/w) eucalyptus oil; (c) about 1.0% to about 10% (w/w) menthol; and (d) about 75% to about 97.5% (w/w) polyethylene glycol, wherein the composition is substantially free of lipids other than the eucalyptus oil. In some embodiments, the composition comprises (a) about 4.8% (w/w) camphor; (b) about 1.2% (w/w) eucalyptus oil; (c) about 2.6% (w/w) menthol; (d) about 30% (w/w) polyethylene glycol 3350; and (e) about 61.4% (w/w) polyethylene glycol 300, wherein the composition is substantially free of lipids other than the eucalyptus oil. In some embodiments, the composition comprises (a) about 4.8% (w/w) camphor; (b) about 1.2% (w/w) eucalyptus oil; (c) about 2.6% (w/w) menthol; (d) about 40%

(w/w) polyethylene glycol 3350; (e) about 40% (w/w) polyethylene glycol 300; and (f) about 11.4% (w/w) water, wherein the composition is substantially free of lipids other than the eucalyptus oil.

In some embodiments, the composition is in a liquid state and comprises (a) about 0.004% to about 0.4% (w/v) camphor; (b) about 0.001% to about 0.5% (w/v) eucalyptus oil; and (c) about 0.001% to about 0.5% (w/w) menthol.

In some embodiments, the compositions of the present inventions are "pharmaceutically acceptable." The term "pharmaceutically acceptable" refers to those compounds, materials, compositions, and/or solutions which are, within the scope of sound medical judgment, suitable specifically for contact with the skin, lips, and nasal mucosal without excessive toxicity, irritation, allergic response, or other problem complications commensurate with a reasonable benefit/risk ratio.

In some embodiments, The compositions of the present inventions are "ophthalmically acceptable." The term "ophthalmically acceptable" refers to those compounds, materials, compositions, and/or solutions which are, within the scope of sound medical judgment, suitable specifically for contact with the tissues of the eye, and the area surrounding the eye without excessive toxicity, irritation, allergic response, or other problem complications commensurate with a reasonable benefit/risk ratio.

The composition of the present invention can be included in a kit. In some embodiment, the present invention is directed to a kit comprising: (a) a composition comprising camphor, eucalyptus oil, and menthol, wherein the composition is substantially free of lipids other than the eucalyptus oil; and (b) instructions for using the composition of (a) for the treatment of epiphora.

The composition can be individually packaged for a single administration, e.g., in a bottle, jar, ampoule, tube, syringe, envelope, container, vial, medicated swab, single-use inhaler, or single-use nasal spray. Alternatively, the composition can be contained in a package that is capable of holding multiple units for administration, e.g., in resealable glass or plastic packages, multi-use nasal spray, or multi-use inhaler. In some kits, the components of the composition are mixed together immediately preceding their usage. For example, in some embodiments one or more dry components of the composition of the kit are packaged in a separate container, e.g., a plastic bottle, and then mixed with one or more of the liquid components of the composition immediately prior to use.

In some embodiments, the present invention is directed to a means for administering the composition of the present invention. The means for administering the composition to the subject can include any apparatus suitable to physically place the composition in close proximity to the nasal area or ocular area, e.g., a stick, spatula, swab, adhesive patch, glove, etc. A means for administering can also include an inhaler, which allows the composition to be directed to a nasal cavity of a subject upon inhalation. In some embodiments, a means for administering can also include nasal spray apparatus, which is suitable for applying the composition in a liquid, mist, or spray to a nasal cavity. Means for administering can also include a nebulizer. In some embodiments, a means for administering can include an eyedropper.

Optionally, the kit can further comprise printed matter containing instructions for using the composition of the present invention. For example, such printed instructions can be in a form prescribed by a governmental agency regulating the manufacture, use or sale of pharmaceuticals or biological products, which reflects approval by the agency of the manufacture, use or sale for human application. In some embodiments, the kit further comprises printed matter, which, e.g., provides information on the use of the composition or a pre-recorded media device which, e.g., provides information on the use of the method of the present invention. "Printed matter" can be, for example, a book, booklet, brochure, leaflet or the like. The printed matter can describe the use of the composition of the present invention.

The kit can also include a container for storing the components of the kit. The container can be, for example, a bag, box, envelope or any other container that would be suitable for use in the present invention. In some embodiments, the container is large enough to accommodate each component of the present invention. However, in some cases, it can be desirable to have a smaller container which is large enough to carry only some of the components of the present invention.

EXAMPLE 1

The gel matrix of the present invention was produced by mixing the ingredients of Table 1.

TABLE 1

| Ingredient | % w/w |
| --- | --- |
| Camphor | 4.8 |
| Eucalyptus Oil | 1.2 |
| Menthol | 2.6 |
| Polyethylene Glycol 3350 | 30 |
| Polyethylene Glycol 300 | 61.4 |

The polyethylene glycol (PEG) components were mixed, melted and heated to give a homogeneous vehicle. The active ingredients (camphor, eucalyptus oil, and menthol) were then added and mixed into the homogeneous vehicle until dissolved. The solution was cooled to room temperature while mixing to maintain homogeneity.

EXAMPLE 2

The composition of Example 1 was administered just inside the external nares of 15 subjects who had bothersome tearing in one or both eyes. The composition was administered one time/day for 14 days. After 14 days, six of the subjects had complete, or near complete, elimination of epiphora, three had some improvement, and six had no improvement. There were no adverse events.

It is to be appreciated that the Detailed Description section, and not the Summary and Abstract sections, is intended to be used to interpret the claims. These examples illustrate possible compositions used in the present invention. While the invention has been particularly shown and described with reference to some embodiments thereof, it will be understood by those skilled in the art that they have been presented by way of example only, and not limitation, and various changes in form and details can be made therein without departing from the spirit and scope of the invention. Thus, the breadth and scope of the present invention should not be limited by any of the above-described exemplary embodiments, but should be defined only in accordance with the following claims and their equivalents.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

What is claimed is:

1. A method for treating epiphora in a subject in need of such treatment, the method comprising administering to a nasal area of the subject a therapeutically effective amount of a composition comprising camphor, eucalyptus oil, and menthol, wherein the composition is substantially free of lipids other than the eucalyptus oil, wherein the epiphora is brought about or exacerbated by a condition selected from the group consisting of punctual stenosis, canicular stenosis, canaliculitis, dacryocystosis, lacrimal sac tumors, congenital malformations of the tear duct system, foreign bodies, inflammation of the tear ducts, eye infections, inability to blink correctly, nerve damage, entropion, ectropion, and age-related changes in the tear drainage system.

2. The method of claim 1, wherein the composition is a gel, cream, ointment, jelly, lotion, or viscous liquid.

3. The method of claim 1, wherein the composition further comprises a viscosity modifying agent.

4. The method of claim 3, wherein the viscosity modifying agent is selected from the group consisting of polyethylene glycol, polyvinyl alcohol, gelatin, hyaluronic acid, carbomer, tragacanth, soluble cellulose derivatives, colloidal magnesium aluminum silicate, sodium alginate, and combinations thereof.

5. The method of claim 4, wherein the viscosity modifying agent is polyethylene glycol.

6. The method of claim 4, wherein the viscosity modifying agent is about 50% to about 95% (w/w) of the composition.

7. The method of claim 1, wherein the camphor is about 1% to about 10% (w/w) of the composition.

8. The method of claim 1, wherein the eucalyptus oil is about 0.5% to about 5% (w/w) of the composition.

9. The method of claim 1, wherein the menthol is about 1% to about 10% (w/w) of the composition.

10. The method of claim 1, wherein the composition is water soluble.

11. The method of claim 1, wherein the composition further comprises an excipient.

12. The method of claim 11, wherein the excipient is about 0.05% to about 20% (w/w) of the composition.

13. The method of claim 12, wherein the excipient is about 0.05% to about 5% (w/w) of the composition.

14. The method of claim 12, wherein the excipient is about 2% to about 10% (w/w) of the composition.

15. The method of claim 1, wherein the composition further comprises a mucoadhesive.

16. The method of claim 15, wherein the mucoadhesive is selected from the group consisting of hydroxypropyl cellulose, hydroxypropyl methylcellulose, hydroxy ethylcellulose, ethylcellulose, carboxymethyl cellulose, dextran, guar gum, polyvinyl pyrrolidone, a pectin, a starch, gelatin, casein, an acrylic acid polymer, a polymer of acrylic acid ester, an acrylic acid copolymer, a vinyl polymer, a vinyl copolymer, a polymer of vinyl alcohol, an alkoxy polymer, a polyethylene oxide polymer, a polyether, and combinations thereof.

17. The method of claim 1, wherein said administering to a nasal area comprises administering to a nasal cavity, external nare, upper lip, philtrum, or combination thereof of the subject in need of such treatment.

18. A method of treating epiphora in a subject in need of such treatment, the method comprising administering to an ocular area of the subject a therapeutically effective amount of a composition comprising camphor, eucalyptus oil, and menthol, wherein the composition is substantially free of lipids or other eucalyptus oil, wherein the epiphora is brought about or exacerbated by a condition selected from the group consisting of punctual stenosis, canicular stenosis, canaliculitis, dacryocystosis, lacrimal sac tumors, congenital malformations of the tear duct system, foreign bodies, inflammation of the tear ducts, eye infections, inability to blink correctly, nerve damage, entropion, ectropion, and age-related changes in the tear drainage system.

19. The method of claim 18, wherein the composition comprises (a) about 0.004% to about 0.4% (w/v) camphor; (b) about 0.001% to about 0.5% (w/v) eucalyptus oil; and (c) about 0.001% to about 0.5% (w/w) menthol.

20. The method of claim 19, wherein the composition is a liquid.

21. The method of claim 1, wherein said composition comprises:
(a) about 1.0% to about 10% (w/w) camphor;
(b) about 0.05% to about 5% (w/w) eucalyptus oil; and
(c) about 1.0% to about 10% (w/w) menthol.

* * * * *